US009119706B2

(12) United States Patent
Daniel et al.

(10) Patent No.: US 9,119,706 B2
(45) Date of Patent: Sep. 1, 2015

(54) INTRAVASCULAR FILTER AND METHOD (75) Inventors: John Daniel, Plymouth, MN (US);
Brian J. Lowe, Fridley, MN (US);
Robert Cassell, Otsego, MN (US);
Bradley F. Slaker, Greenfield, MN (US); John E. Arnold, Jr., Minneapolis, MN (US); Thomas E. Broome, Hopkins, MN (US)

(73) Assignee: BOSTON SCIENTIFIC SCIMED INC., Maple Grove, MN (US)

( * ) Notice: Subject to any disclaimer, the term of this patent is extended or adjusted under 35 U.S.C. 154(b) by 1102 days.

(21) Appl. No.: 12/572,769

(22) Filed: Oct. 2, 2009

(65) Prior Publication Data

US 2010/0023049 A1    Jan. 28, 2010

Related U.S. Application Data (63) Continuation of application No. 10/391,261, filed on Mar. 18, 2003, now Pat. No. 7,618,433, which is a continuation of application No. 09/722,931, filed on Nov. 27, 2000, now Pat. No. 6,544,280, which is a continuation of application No. 09/256,865, filed on Feb. 24, 1999, now Pat. No. 6,171,327.

(51) Int. Cl.
*A61F 2/01*    (2006.01)

(52) U.S. Cl.
CPC . *A61F 2/013* (2013.01); *A61F 2/01* (2013.01); *A61F 2002/011* (2013.01); *A61F 2002/018* (2013.01); *A61F 2230/0006* (2013.01); *A61F 2230/0067* (2013.01); *A61F 2250/0023* (2013.01); *A61F 2250/0098* (2013.01)

(58) Field of Classification Search
USPC ................. 606/200, 113, 114; 623/1.11, 1.23
See application file for complete search history.

(56) References Cited

U.S. PATENT DOCUMENTS

| | | |
|---|---|---|
| 3,472,230 A | 10/1969 | Fogarty |
| 3,592,186 A | 7/1971 | Oster |
| 3,683,904 A | 8/1972 | Forster |
| 3,889,657 A | 6/1975 | Baumgarten et al. |
| 3,952,747 A | 4/1976 | Kimmell, Jr. |
| 3,996,938 A | 12/1976 | Clark, III |
| 4,046,150 A | 9/1977 | Schwartz et al. |
| 4,425,908 A | 1/1984 | Simon |

(Continued)

FOREIGN PATENT DOCUMENTS

| | | |
|---|---|---|
| DE | 2821048 B1 | 11/1979 |
| DE | 3417738 A1 | 11/1985 |

(Continued)

OTHER PUBLICATIONS

"Atherosclerotic Disease of the Aortic Arch as a Risk Factor of Recurrent Ischemic Stroke," The New England Journal of Medicine, pp. 1216-1221 (May 1996).

(Continued)

*Primary Examiner* — Tuan V Nguyen
(74) *Attorney, Agent, or Firm* — Seager, Tufte & Wickhem LLP (57) ABSTRACT A filter disposed at the distal end of an elongate guidewire. Catheters are provided for delivering the filter to, and retrieving the filter from, a treatment site. The catheters can be over-the-wire or single operator exchange. The catheters include a housing for receiving the filter therein. The housing has an atraumatic distal end.

8 Claims, 8 Drawing Sheets (56) References Cited

U.S. PATENT DOCUMENTS

| | | |
|---|---|---|
| 4,447,227 A | 5/1984 | Kotsanis |
| 4,580,568 A | 4/1986 | Gianturco |
| 4,590,938 A | 5/1986 | Segura et al. |
| 4,619,246 A | 10/1986 | Molgaard-Nielsen et al. |
| 4,631,052 A | 12/1986 | Kensey |
| 4,643,184 A | 2/1987 | Mobin-Uddin |
| 4,650,466 A | 3/1987 | Luther |
| 4,662,885 A | 5/1987 | DiPisa, Jr. |
| 4,705,517 A | 11/1987 | DiPisa, Jr. |
| 4,706,671 A | 11/1987 | Weinrib |
| 4,723,549 A | 2/1988 | Wholey et al. |
| 4,728,319 A | 3/1988 | Masch |
| 4,733,665 A | 3/1988 | Palmaz |
| 4,790,812 A | 12/1988 | Hawkins, Jr. et al. |
| 4,790,813 A | 12/1988 | Kensey |
| 4,794,928 A | 1/1989 | Kletschka |
| 4,794,931 A | 1/1989 | Yock |
| 4,800,882 A | 1/1989 | Gianturco |
| 4,807,626 A | 2/1989 | McGirr |
| 4,842,579 A | 6/1989 | Shiber |
| 4,857,045 A | 8/1989 | Rydell |
| 4,857,046 A | 8/1989 | Stevens et al. |
| 4,867,157 A | 9/1989 | McGurk-Burleson et al. |
| 4,873,978 A | 10/1989 | Ginsburg |
| 4,898,575 A | 2/1990 | Fischell et al. |
| 4,907,336 A | 3/1990 | Gianturco |
| 4,921,478 A | 5/1990 | Solano et al. |
| 4,921,484 A | 5/1990 | Hillstead |
| 4,926,858 A | 5/1990 | Gifford et al. |
| 4,950,277 A | 8/1990 | Farr |
| 4,955,895 A | 9/1990 | Sugiyama et al. |
| 4,957,482 A | 9/1990 | Shiber |
| 4,969,891 A | 11/1990 | Gewertz |
| 4,979,951 A | 12/1990 | Simpson |
| 4,986,807 A | 1/1991 | Farr |
| 4,998,539 A | 3/1991 | Delsanti |
| 5,002,560 A | 3/1991 | Machold |
| RE33,569 E | 4/1991 | Gifford, III et al. |
| 5,007,896 A | 4/1991 | Shiber |
| 5,007,917 A | 4/1991 | Evans |
| 5,011,488 A | 4/1991 | Ginsburg |
| 5,019,088 A | 5/1991 | Farr |
| 5,041,126 A | 8/1991 | Gianturco |
| 5,053,008 A | 10/1991 | Bajaj |
| 5,053,044 A | 10/1991 | Mueller et al. |
| 5,071,407 A | 12/1991 | Termin et al. |
| 5,071,425 A | 12/1991 | Gifford, III et al. |
| 5,085,662 A | 2/1992 | Willard |
| 5,087,265 A | 2/1992 | Summers |
| 5,100,423 A | 3/1992 | Fearnot |
| 5,100,424 A | 3/1992 | Jang et al. |
| 5,100,425 A | 3/1992 | Fischell |
| 5,102,415 A | 4/1992 | Guenther |
| 5,104,399 A | 4/1992 | Lazarus |
| 5,108,419 A | 4/1992 | Reger et al. |
| 5,133,733 A | 7/1992 | Rasmussen et al. |
| 5,135,531 A | 8/1992 | Shiber |
| 5,152,771 A | 10/1992 | Sabbaghian et al. |
| 5,152,777 A | 10/1992 | Goldberg et al. |
| 5,160,342 A | 11/1992 | Reger et al. |
| 5,171,233 A | 12/1992 | Amplatz et al. |
| 5,190,546 A | 3/1993 | Jervis |
| 5,195,955 A | 3/1993 | Don Michael |
| 5,224,953 A | 7/1993 | Morgentaler |
| 5,306,286 A | 4/1994 | Stack et al. |
| 5,314,444 A | 5/1994 | Gianturco |
| 5,314,472 A | 5/1994 | Fontaine |
| 5,318,576 A | 6/1994 | Plassche, Jr. et al. |
| 5,329,942 A | 7/1994 | Gunther et al. |
| 5,330,484 A | 7/1994 | Gunther |
| 5,330,500 A | 7/1994 | Song |
| 5,350,398 A | 9/1994 | Pavcnik et al. |
| 5,354,310 A | 10/1994 | Garnic et al. |
| 5,356,423 A | 10/1994 | Tihon et al. |
| 5,366,464 A | 11/1994 | Belknap |
| 5,366,473 A | 11/1994 | Winston et al. |
| 5,370,657 A | 12/1994 | Irie |
| 5,370,683 A | 12/1994 | Fontaine |
| 5,376,100 A | 12/1994 | Lefebvre |
| 5,383,887 A | 1/1995 | Nadal |
| 5,383,892 A | 1/1995 | Cardon et al. |
| 5,383,926 A | 1/1995 | Lock et al. |
| 5,387,235 A | 2/1995 | Chuter |
| 5,395,349 A | 3/1995 | Quiachon et al. |
| 5,397,345 A | 3/1995 | Lazarus |
| 5,403,341 A * | 4/1995 | Solar ............................ 606/198 |
| 5,405,377 A | 4/1995 | Cragg |
| 5,409,454 A | 4/1995 | Fischell et al. |
| 5,415,630 A | 5/1995 | Gory |
| 5,419,774 A | 5/1995 | Willard et al. |
| 5,421,832 A | 6/1995 | Lefebvre |
| 5,423,742 A | 6/1995 | Theron |
| 5,423,885 A | 6/1995 | Williams |
| 5,425,765 A | 6/1995 | Tiefenbrun et al. |
| 5,443,498 A | 8/1995 | Fontaine |
| 5,449,372 A | 9/1995 | Schmaltz et al. |
| 5,456,667 A | 10/1995 | Ham et al. |
| 5,462,529 A | 10/1995 | Simpson |
| 5,476,104 A | 12/1995 | Sheahon |
| 5,484,418 A | 1/1996 | Quiachon et al. |
| 5,507,767 A | 4/1996 | Maeda et al. |
| 5,512,044 A | 4/1996 | Duer |
| 5,527,354 A | 6/1996 | Fontaine et al. |
| 5,536,242 A | 7/1996 | Willard et al. |
| 5,540,707 A | 7/1996 | Ressemann et al. |
| 5,549,626 A | 8/1996 | Miller et al. |
| 5,562,724 A | 10/1996 | Vorwerk et al. |
| 5,569,274 A | 10/1996 | Rapacki et al. |
| 5,569,275 A | 10/1996 | Kotula et al. |
| 5,634,897 A | 6/1997 | Dance et al. |
| 5,658,296 A | 8/1997 | Bates et al. |
| 5,662,671 A | 9/1997 | Barbut et al. |
| 5,669,933 A | 9/1997 | Simon et al. |
| 5,695,519 A | 12/1997 | Summers et al. |
| 5,709,704 A | 1/1998 | Nott et al. |
| 5,720,764 A | 2/1998 | Naderlinger |
| 5,728,066 A | 3/1998 | Daneshvar |
| 5,746,758 A | 5/1998 | Nordgren |
| 5,749,848 A | 5/1998 | Jang et al. |
| 5,769,816 A * | 6/1998 | Barbut et al. ............... 604/93.01 |
| 5,779,716 A | 7/1998 | Cano |
| 5,792,157 A | 8/1998 | Mische et al. |
| 5,792,300 A | 8/1998 | Inderbitzen |
| 5,795,322 A | 8/1998 | Boudewijn |
| 5,797,952 A | 8/1998 | Klein |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,817,102 A | 10/1998 | Johnson et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,893,867 A | 4/1999 | Bagaoisan et al. |
| 5,895,399 A | 4/1999 | Barbut et al. |
| 5,902,263 A | 5/1999 | Patterson et al. |
| 5,906,618 A | 5/1999 | Larson |
| 5,908,435 A | 6/1999 | Samuels |
| 5,910,154 A | 6/1999 | Tsugita et al. |
| 5,911,734 A | 6/1999 | Tsugita et al. |
| 5,916,193 A | 6/1999 | Stevens et al. |
| 5,925,016 A | 7/1999 | Chornenky |
| 5,925,060 A | 7/1999 | Forber |
| 5,925,062 A | 7/1999 | Purdy |
| 5,925,063 A | 7/1999 | Khosravi |
| 5,928,203 A | 7/1999 | Davey et al. |
| 5,928,218 A | 7/1999 | Gelbfish |
| 5,934,284 A | 8/1999 | Plaia et al. |
| 5,935,139 A | 8/1999 | Bates |
| 5,938,645 A | 8/1999 | Gordon |
| 5,941,869 A | 8/1999 | Patterson et al. |

(56) References Cited

U.S. PATENT DOCUMENTS

| | | |
|---|---|---|
| 5,941,896 A | 8/1999 | Kerr |
| 5,947,995 A | 9/1999 | Samuels |
| 5,951,585 A | 9/1999 | Cathcart et al. |
| 5,976,172 A | 11/1999 | Homsma |
| 5,980,555 A | 11/1999 | Barbut et al. |
| 5,989,271 A | 11/1999 | Bonnette et al. |
| 5,989,281 A | 11/1999 | Barbut et al. |
| 5,993,469 A | 11/1999 | McKenzie |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson |
| 6,068,645 A | 5/2000 | Tu |
| 6,086,605 A | 7/2000 | Barbut et al. |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,165,200 A | 12/2000 | Tsugita et al. |
| 6,168,579 B1 | 1/2001 | Tsugita |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer |
| 6,309,399 B1 | 10/2001 | Barbut et al. |
| 6,319,268 B1 | 11/2001 | Ambrisco et al. |
| 6,344,049 B1 | 2/2002 | Levinson et al. |
| 6,371,969 B1 | 4/2002 | Tsugita et al. |
| 6,544,280 B1 | 4/2003 | Daniel et al. |
| 6,606,102 B1 | 8/2003 | Odom |
| 7,618,433 B2 | 11/2009 | Daniel et al. |
| 2002/0161394 A1 | 10/2002 | Macoviak et al. |

FOREIGN PATENT DOCUMENTS

| | | |
|---|---|---|
| DE | 4030998 A1 | 4/1991 |
| DE | 19916162 A1 | 10/2000 |
| EP | 0200688 A1 | 11/1986 |
| EP | 0293605 A1 | 12/1988 |
| EP | 0411118 A1 | 2/1991 |
| EP | 0427429 A2 | 5/1991 |
| EP | 0472334 A1 | 2/1992 |
| EP | 0472368 A2 | 2/1992 |
| EP | 0533511 A1 | 3/1993 |
| EP | 0655228 A1 | 11/1994 |
| EP | 0686379 A2 | 12/1995 |
| EP | 0696447 A2 | 2/1996 |
| EP | 0737450 A1 | 10/1996 |
| EP | 0743046 A1 | 11/1996 |
| EP | 0759287 A1 | 2/1997 |
| EP | 0771549 A2 | 5/1997 |
| EP | 0784988 A1 | 7/1997 |
| EP | 0437121 B1 | 8/1997 |
| EP | 0852132 A1 | 7/1998 |
| EP | 0934729 A1 | 8/1999 |
| EP | 1127556 A2 | 8/2001 |
| FR | 2580504 A1 | 10/1986 |
| FR | 2643250 A1 | 8/1990 |
| FR | 2666980 A1 | 3/1992 |
| FR | 2694687 A1 | 2/1994 |
| FR | 2768326 A1 | 3/1999 |
| GB | 2020557 B | 1/1983 |
| JP | 8187294 A2 | 7/1996 |
| SU | 764684 A | 9/1980 |
| WO | 9203097 A1 | 3/1992 |
| WO | 9414389 A1 | 7/1994 |
| WO | 9424946 A1 | 11/1994 |
| WO | 9601591 A1 | 1/1996 |
| WO | 9610375 A1 | 4/1996 |
| WO | 9619941 A1 | 7/1996 |
| WO | 9623441 A1 | 8/1996 |
| WO | 9633677 A1 | 10/1996 |
| WO | 9717100 A1 | 5/1997 |
| WO | 9727808 A1 | 8/1997 |
| WO | 9742879 A1 | 11/1997 |
| WO | 9802084 A2 | 1/1998 |
| WO | 9802112 A1 | 1/1998 |
| WO | 9823322 A1 | 6/1998 |
| WO | 9834673 A1 | 8/1998 |
| WO | 9836786 A1 | 8/1998 |
| WO | 9838920 A1 | 9/1998 |
| WO | 9838929 A1 | 9/1998 |
| WO | 9839046 A1 | 9/1998 |
| WO | 9839053 A1 | 9/1998 |
| WO | 9846297 A1 | 10/1998 |
| WO | 9847447 A1 | 10/1998 |
| WO | 9849952 A1 | 11/1998 |
| WO | 9850103 A1 | 11/1998 |
| WO | 9851237 A1 | 11/1998 |
| WO | 9855175 A1 | 12/1998 |
| WO | 9909895 A1 | 3/1999 |
| WO | 9922673 A1 | 5/1999 |
| WO | 9923976 A1 | 5/1999 |
| WO | 9925252 A1 | 5/1999 |
| WO | 9930766 A1 | 6/1999 |
| WO | 9940964 A1 | 8/1999 |
| WO | 9942059 A1 | 8/1999 |
| WO | 9944510 A1 | 9/1999 |
| WO | 9955236 A1 | 11/1999 |
| WO | 9958068 A2 | 11/1999 |
| WO | 0007521 A1 | 2/2000 |
| WO | 0007655 A1 | 2/2000 |
| WO | 0009054 A1 | 2/2000 |
| WO | 0016705 A1 | 3/2000 |
| WO | 0049970 A1 | 8/2000 |
| WO | 0053120 A1 | 9/2000 |
| WO | 0067664 A1 | 11/2000 |
| WO | 0067665 A1 | 11/2000 |
| WO | 0067666 A1 | 11/2000 |
| WO | 0067668 A1 | 11/2000 |
| WO | 0067669 A1 | 11/2000 |
| WO | 0105462 A1 | 1/2001 |
| WO | 0108595 A1 | 2/2001 |
| WO | 0108596 A1 | 2/2001 |
| WO | 0108742 A1 | 2/2001 |
| WO | 0108743 A1 | 2/2001 |
| WO | 0110320 A1 | 2/2001 |
| WO | 0115629 A1 | 3/2001 |
| WO | 0121077 A1 | 3/2001 |
| WO | 0121100 A1 | 3/2001 |
| WO | 0126726 A1 | 4/2001 |

(56) References Cited

FOREIGN PATENT DOCUMENTS

| WO | 0135857 A1 | 5/2001 |
|---|---|---|
| WO | 0143662 A1 | 6/2001 |
| WO | 0147579 A1 | 7/2001 |
| WO | 0149208 A1 | 7/2001 |
| WO | 0149209 A1 | 7/2001 |
| WO | 0149215 A2 | 7/2001 |
| WO | 0149355 A1 | 7/2001 |
| WO | 0152768 A1 | 7/2001 |
| WO | 0158382 A2 | 8/2001 |
| WO | 0160442 A1 | 8/2001 |
| WO | 0167989 A2 | 9/2001 |
| WO | 0170326 A1 | 9/2001 |
| WO | 0172205 A2 | 10/2001 |
| WO | 0187183 A2 | 11/2001 |
| WO | 0189413 A2 | 11/2001 |
| WO | 0191824 A2 | 12/2001 |

OTHER PUBLICATIONS

"Endovascular Grafts, Stents Drive Interventional Radiology Growth," Cardiovascular Device Update, 2(3):1-12 (Mar. 1996).
"Protruding Atheromas in the Thoracic Aortic and Systemic Embolization," pp. 423-427 American College of Physicians (1991).
"Recognition and Embolic Potential of Intraaortic Atherosclerotic Debris," American College of Cardiology (Jan. 1991).
Cragg, Andrew et al., "A New Percutaneous Vena Cava Filger," AJR, 141:601-604 (Sep. 1983).
Cragg, Andrew et al., "Nonsurgical Placement of Arterial Endoprosthesis: A New Technique Using Nitinol Wire," AJR, pp. 261-263 (Apr. 1983).
Diethrich et al., "Percutaneous Techniques for Endoluminal Carotid Interventions," J. Endovasc. Surg., 3:182-202 (1996).
Fadali, A. Moneim, "A filtering device for the prevention of particulate embolization during the course of cardiac surgery," Surgery, 64(3):634-639 (Sep. 1968).
Haissaguerre et al., "Spontaneous Initiation of Atrial Fibrillation by Ectopic Beats Originating in the Pulmonary Veins," The New England Journal of Medicine, 339(10):659-666 (Sep. 1988).
Jordan, Jr. et al., "Microemboli Detected by Transcranial Doppler Monitoring . . . ," Cardiovascular Surgery, 7(1)33-38 (Jan. 1999).
Lesh, "Can Catheter Ablation Cure Atrial Fibrillation?" ACC Current Journal Review, pp. 38-40 (Sep./Oct. 1997).
Lund et al., "Long-Term Patentcy of Ductus Arteriosus After Balloon Dilation: an Experimental Study," Laboratory Investigation, 69(4):772-774 (Apr. 1984).
Marache et al., "Percutaneous Transluminal Venous Angioplasty . . . ," American Heart Journal, 125(2 Pt 1):362-366 (Feb. 1993).
Mazur et al., "Directional Atherectomy with the Omnicath™: A Unique New Catheter System," Catheterization and Cardiovascular Diagnosis, 31:17-84 (1994).
Moussa, MD, Issaam "Stents Don't Require Systemic Anticoagulation . . . But the Technique (and Results) Must be Optimal," Journal of Invasive Cardiol., 8(E):3E-7E, (1996).
Nakanishi et al., "Catheter Intervention to Venous System Using Expandable Metallic Stents," Rinsho Kyobu Geka, 14 (2):English Abstract Only (Apr. 1994).
Onal et al., "Primary Stenting for Complex Atherosclerotic Plaques in Aortic and Iliac Stenoses," Cardiovascular & Interventional Radiology, 21(5):386-392 (1998).
Theron et al., "New Triple Coaxial Catheter System for Carotid Angioplasty with Cerebral Protection," American Journal of Neuroradiology, 11:869-874 (1990).
Tunick et al., "Protruding atherosclerotic plaque in the aortic archo f patients with systemic embolization: A new finding seen by transesophageal echocardiography," American Heart Journal120(3):658-660 (Sep. 1990).
Waksman et al., "Distal Embolization is Common After Directional Atherectomy . . . ," American Heart Journal, 129 (3):430-435 (1995).
Wholey, Mark H. et al., PTA and Stents in the Treatment of Extracranial Circulation, The Journal of Invasive Cardiology, 8(E):25E-30E (1996).

\* cited by examiner

INTRAVASCULAR FILTER AND METHOD

RELATED APPLICATIONS

This application is a continuation of U.S. patent application Ser. No. 10/391,261 filed on Mar. 18, 2003, now U.S. Pat. No. 7,618,433; which in turn is a continuation of U.S. patent application Ser. No. 09/722,931 filed on Nov. 27, 2000, now U.S. Pat. No. 6,544,280; which in turn is a continuation of U.S. patent application Ser. No. 09/256,865 filed on Feb. 24, 1999, now U.S. Pat. No. 6,171,327.

BACKGROUND OF THE INVENTION

The present invention relates to the field of minimally invasive, percutaneous procedures such as angioplasty. In particular, the invention relates to a distal filter for use during such a procedure.

Angioplasty, atherectomy and stent placement, among other procedures, have become well accepted for treatment of coronary lesions. These procedures are often performed as an alternative to coronary bypass. It is also possible, however, that a saphenous vein graft, which is used to bypass coronary lesions, may itself develop a lesion. These lesions may also be treated by minimally invasive procedures such as angioplasty, atherectomy and/or stent placement.

When lesions are treated by these minimally invasive, percutaneous methods, it is possible that particles of plaque, thrombus or other material may break loose from the lesion and drift distally into the smaller coronary arteries. When these minimally invasive methods are performed on native arteries, the plaque or thrombus released during the procedure rarely cause embolization. When these procedures are performed on saphenous vein grafts, however, the incidence of embolism due to the breaking off of plaque or thrombus from the vein graft is substantially greater than from native arteries.

The increased incidence of embolization is believed to be due, at least in part, to the larger diameter of the bypass graft relative to the native artery. The larger diameter of the graft results in a slower blood flow velocity through the graft than the native artery. In addition, the plaque and thrombus of vein grafts is somewhat more fragile than that found in native arteries.

As the difference in embolism associated with treatment of native arteries and vein grafts has been noted, it would be desirable to develop techniques to reduce embolism associated with treatment of vein graft lesions. Additionally, where stent placement or other minimally invasive treatments are performed on the carotid artery, it would be desirable to limit the drift of plaque and thrombus toward the brain.

SUMMARY OF THE INVENTION

The present invention pertains to an intravascular filter for use during minimally invasive percutaneous procedures. The filter is preferably placed distally, within the blood stream, of the site of the interventional procedure. The filter may be used to filter plaque, thrombus and other debris released into the blood stream during minimally invasive procedures performed in blood vessels.

A filter assembly in accordance with the present invention includes a catheter including an elongate shaft having a proximal end and a distal end. A housing is disposed at the distal end of the shaft. The housing itself has a distal end. An elongate wire extends at least in part through the catheter. The wire has a proximal end and a distal end. A filter is connected to the wire proximate the distal end of the wire. The filter, during delivery and retrieval from its deployment site is preferably at least, in part, disposed within the housing.

By retracting the catheter relative to the filter, the filter emerges from within the housing to a position outside the housing for deployment of the filter. When the filter is disposed outside the housing, the filter can be drawn into the housing by pushing the housing over the filter. It is preferable, however, to retrieve the filter with a different catheter having a housing having a larger inside diameter than the housing of the catheter used to deliver the filter.

It is preferable that the distal end of the housing be atraumatic. This can be accomplished by using a soft atraumatic material for the filter distal end. Additionally, if the catheter is a delivery catheter, the distal end can also be tapered by heat shrinking the distal end of the housing around a portion of the filter. The filter itself can also be slightly wider than the distal end of the housing such that the filter acts as an atraumatic distal end of the filter assembly. The distal end of the housing can also be rounded inwardly toward the filter. In yet another embodiment, the distal end of the housing can include an elastomeric sheath which tapers distally. In still another embodiment of the filter assembly, a collapsible shell can be connected to the wire. The shell is preferably disposed substantially distally of the filter. The wire can include a spring tip.

Where the catheter is a retrieval catheter, a housing atraumatic tip insert can be disposed within the housing and extend distally therefrom while the filter is positioned outside the housing. The insert preferably tapers distally. In one embodiment, the insert can be releasably connected to the distal end of the housing. In a preferred embodiment, the insert includes a balloon. In yet another embodiment, the insert includes a flap which extends transversely over the distal end of the housing. When the filter is withdrawn into the housing, the insert is drawn proximally into the housing as well.

The elongate shaft of the filter assembly can have an elongate wire lumen running through its length. In such a configuration, the catheter can be considered an over-the-wire catheter. The catheter can be converted to a single operator exchange catheter by dividing the shaft into two or more elongate segments and coupling the segments together. The length of the segments should be such that they can be uncoupled or coupled as they are being withdrawn or advanced over the wire. The coupling could include a bayonet fastener or a threaded fastener for example. As an alternative to the coupling, the catheter can be configured for a single operator exchange by providing a telescoping or collapsible portion. The collapsible portion can include a member which can have a braided portion. In an alternate embodiment, the catheter can include longitudinal slits for removal of the catheter from the wire.

The filter itself is disposed at the distal end of the wire. The filter includes an expandable frame and filter membrane. The frame can include a nickel titanium alloy. The membrane preferably surrounds a portion of the wire and is configured to taper distally. The membrane preferably includes polyurethane and defines a plurality of apertures. Once the filter is deployed distally of the lesion to be treated, the wire can be used as a guidewire for advancing angioplasty, atherectomy, or other devices thereover.

DETAILED DESCRIPTION OF THE INVENTION

Figure 1:
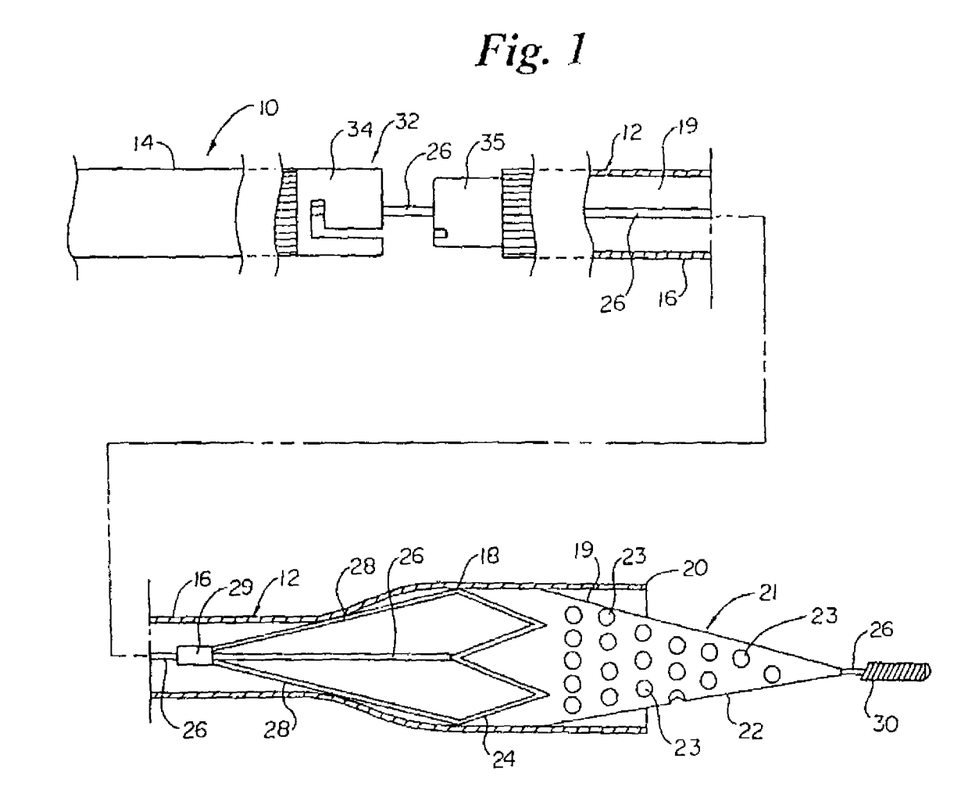
FIG. 1 is a partial cross sectional side view of a delivery catheter and filter in accordance with the present invention.

Referring now to the drawings wherein like reference numerals refer to like elements throughout the several views, FIG. 1 is a partial cross sectional, side view of a filter assembly 10 in accordance with the present invention. Filter assembly 10 includes a delivery catheter 12. Delivery catheter 12 can include a proximal section 14 coupled to a distal section 16. Disposed at the distal end of catheter 12 is a filter housing 18. Filter housing 18 has a distal end 20. As known to those skilled in the art, a manifold having guide wire and side ports can be disposed at the proximal end of catheter 12.

Catheter 12 preferably defines a lumen 19 extending therethrough. In the region of housing 18, lumen 19 preferably has a diameter of between 2 F to 5 F and more preferably, between 3 F to 4 F and most preferably, about 3 F. The diameter of lumen 19 in shaft sections 14 and 16 is preferably between 2 F and 5 F and most preferably, about 2 F.

The length of the delivery catheter is preferably sufficient to reach a treatment site in a coronary artery or graft from a femoral approach. It can be appreciated, however, that if an alternate approach such as a brachial approach is taken, or an alternative target site is desired, the length of the catheter should be appropriate to the specific use.

The catheter can be manufactured from any of the appropriate biocompatible materials from which one skilled in the art would be aware. Shaft portions 14 and 16 should be made from a material sufficiently rigid, yet flexible to be advanced through a tortuous path to a target site. Marker bands can be placed on catheter 12 to guide the placement of filter 21.

Disposed and compressed within catheter 10 is a filter 21. Filter 21 includes a membrane 22 disposed in a generally conical arrangement. Membrane 22 defines a plurality of apertures 23 extending therethrough. Filter 21 also includes a frame 24 which preferably is formed from a zigzag member which in a transverse cross section through housing 18 has a generally circular cross section. The collapsed diameter of frame 24 is preferably about the same but less than the inside diameter of lumen 19 at housing 18. The length of membrane 22 between frame 24 and wire 26 is preferably between about 5 mm and 50 mm, and more preferably between 10 mm and 30 mm, and most preferably approximately 20 mm. Filter membrane 22 is adhered to zigzag frame member 24 by a solvent casting method, wherein the liquid membrane polymer is dipped over the zigzag frame and allowed to cure and solidify.

Filter 21, including membrane 22 and frame 24 are attached to a wire 26 which extends the length of catheter 12. The proximal end of filter 21 is connected to wire 26 by two or more tails 28 extending from frame 24 to a stop 29. Stop 29 can be a clamp or wire winding, solder or other connector. At the distal end of filter 21, membrane 22 may be adhered to wire 26 by a suitable adhesive such as, for example, cyanoacrylates. A coil tip 30 such as one known to those skilled in the art is preferably disposed at the distal end of wire 26.

Figure 2:
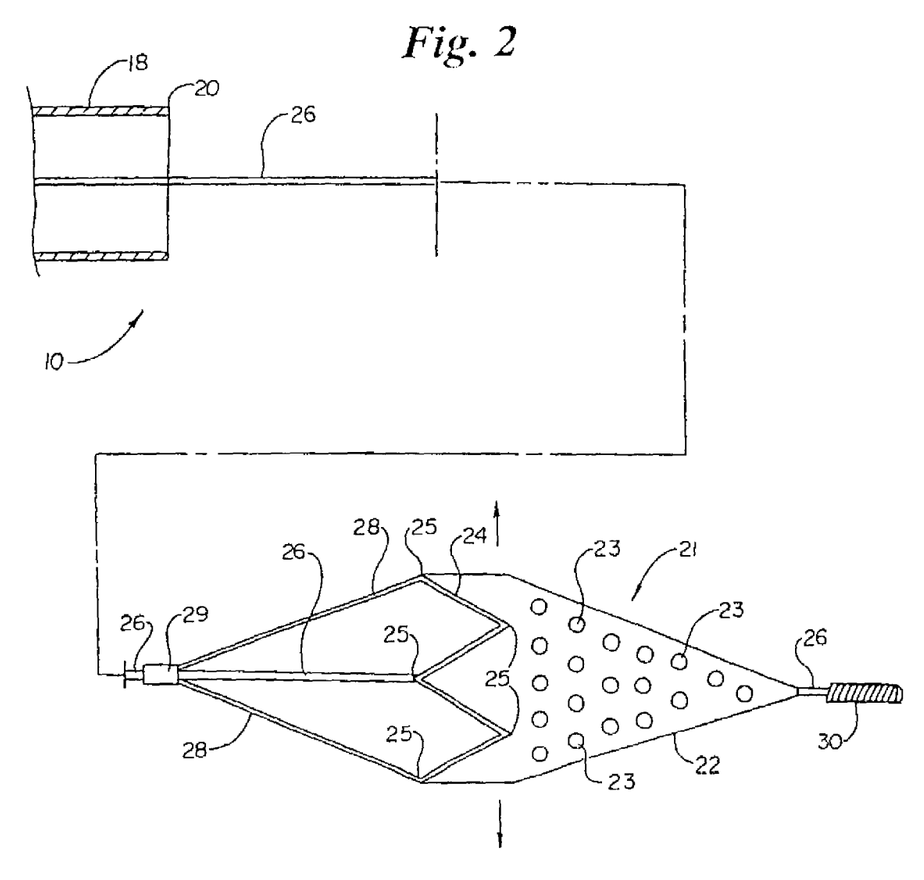
FIG. 2 is a partial cross sectional view of the catheter and filter of FIG. 1 wherein the filter is advanced distally from the catheter.

Wire 26 is preferably formed from stainless steel, NiTi alloy and/or other suitable biocompatible materials known to those skilled in the art of guidewire construction. Wire 26 can also include a radiopaque marker band or plating to aid in the placement of filter 21. Frame 24 and tails 28 are preferably formed from an NiTi alloy such as Nitinol, but can comprise stainless steel or other suitable materials. Frame 24 is preferably heat set to expand to the configuration shown in FIG. 2 when exposed to approximately body temperature.

Membrane 22 of filter 21 preferably has a thickness of between 25 microns and 100 microns and most preferably about 40 microns. The filter is preferably formed from polyurethane or other biocompatible material such as, for example, polyesters or silicones. The filter can be coated with various coatings to impart various functional performance characteristics, one example being a thrombus resistant coating such as Heparin to discourage clot formation on filter 21. Apertures 23 can be drilled in a precise pattern using excimer laser or other ablation techniques or by mechanical techniques.

The size of apertures 23 can vary along the length of filter 21 for example, larger apertures may be placed more proximally and smaller apertures more distally or vice versa. The size of the apertures may transition gradually or abruptly in a proximal or distal direction. The apertures shape can vary from circular shaped to rectangular, square, trapezoidal, oval, slit or other shape. A circular aperture may have a diameter of, for example, 100 microns whereas a slit may have a width of 100 microns and a length of 300 microns. The edges of the apertures can be mechanically or chemically chamfered, etched or polished to provide a smooth and rounded shoulder to streamline the passage of blood from within the conical shape portion of the filter to outside of the filter. To limit thrombus formation, the apertures size and design should be such that the shear forces that blood components are exposed to are appropriate while blood is passing through the filter. Thus, aperture sizes should be selected to limit stagnation and re-circulation of blood in and around the filter while the filter is in use.

Catheter 12 can be formed in two or more sections such as proximal section 14 and distal section 16. These sections can be releasably coupled together by way of a bayonet coupling 32 having a male portion 34 and female portion 35. Alternately, a threaded coupling could be used. As will be explained in more detail below by providing the ability to separate catheter 12 into several sections, catheter 12 can be used as a single operator exchange device.

In use, assembly 10 is advanced to a treatment site such as a coronary saphenous vein bypass graft by way of, for example, a femoral approach such that housing 18 and filter 21 is disposed distally of a lesion to be treated. Catheter 12 is then withdrawn distally such that filter 21 can expand in the direction shown by the arrows in FIG. 2. Filter 21 should be allowed to expand such that it substantially traverses the cross sectional area of the vessel.

If catheter 12 is divided into sections such as section 14 and 16, catheter 12 can be completely removed from the body over a wire 26 having a standard guidewire length of about 180 cm for a femoral approach to a coronary artery or graft. First proximal section 14 is backed out of the body while holding the proximal end of wire 26 as coupling 32 emerges from the body. Section 14 is uncoupled from section 16 exposing wire 26 therebetween. Wire 26 disposed between section 14 and 16 can then be grasped and section 14 removed proximally from wire 26. Section 16 and housing 18 can subsequently be removed proximally from wire 26. The length of sections 14 and 16 and the length of wire 26 are preferably such that a physician can at all times during removal of catheter 12 grasp a portion of wire 26 disposed outside of the patient's body. It should be understood, however, that catheter 12 need not be a single operator exchange catheter but rather can be an over-the-wire catheter or other type as known to those skilled in the art.

Once catheter 12 has been removed from wire 26, wire 26 can be used as a guidewire for advancing surgical instruments thereover. For example, an angioplasty balloon could be advanced over wire 26 to a location just proximal of filter 21. While filter 21 is deployed, angioplasty can be performed. Plaque and thrombus dislodged by the procedure will then drift distally into filter 21. It is anticipated that other procedures will be preformed in this way including, for example, atherectomy and stent placement.

Figure 3:
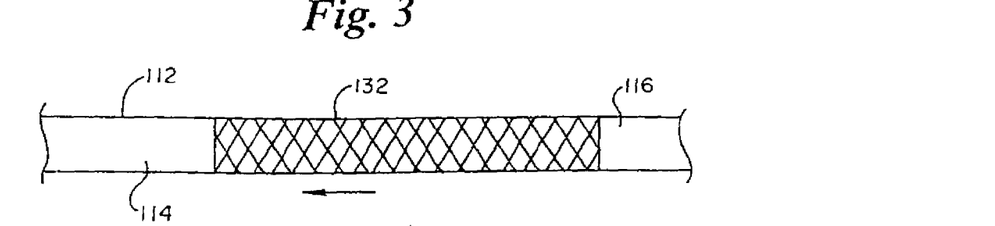
FIG. 3 is a view of a shaft of a catheter in accordance with the present invention including a collapsible portion.
Figure 4:
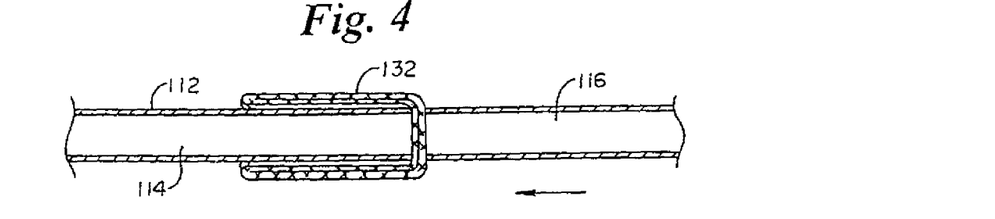
FIG. 4 is a view of the shaft of FIG. 3 wherein the collapsible portion is collapsed.

FIG. 3 is a side view of an alternate catheter 112 having a proximal shaft section 114 and a distal shaft section 116. Proximal shaft section 114 is connected to distal shaft section 116 by a highly flexible or braided section 132. When catheter 112 is withdrawn in the direction of the arrow, braided section 132 is drawn tight for removal from wire 26 and filter 21 as explained above with respect to catheter 12. As proximal shaft portion 114 is withdrawn proximally, braided section 132 will be exposed outside of the body. Distal section 116 can then be advanced proximately relative to proximal section 114 as shown in FIG. 4. Braided section 132 can then be collapsed to shorten the overall length of catheter 112. The length of sections 114, 116 and 132 relative to wire 26 should be such that wire 26 can be grasped by a physician at all times during removal of catheter 112.

Figures 5, 6:
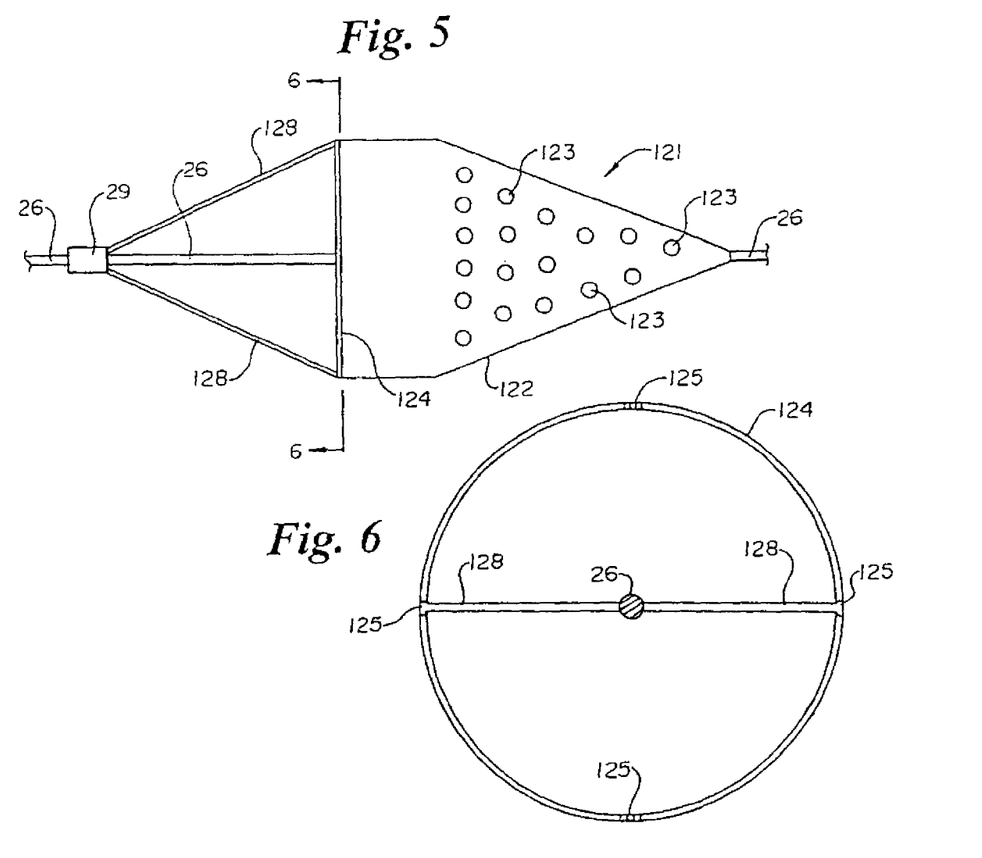
FIG. 5 is a view of an alternate embodiment of the filter in accordance with the present invention.
FIG. 6 is a cross sectional view of the filter of FIG. 5.

FIG. 5 is a side view of an alternate filter 121 in accordance with the present invention. Like filter 21, filter 121 includes a membrane 122 defining a plurality of apertures 123. Filter 121 also includes a conical portion formed by a portion of membrane 122 surrounding wire 26. Filter 121 also includes a generally cylindrical portion which at its proximal end is connected to a generally circular frame 124. Two or more tails 128 extend from frame 124 to wire 26. Tails 128 are attached to wire 26 at stop 29. Membrane 122 is attached to frame 124 by a solvent casting method as explained previously with respect to filter 21. A cyanoacrylate or epoxy adhesive can be used to connect the distal end of filter 121 to wire 26. The materials of construction for the filter can be selected from those described above with respect to filter 21. For example, frame 124 can be formed from NiTi alloys such as Nitinol and membrane 122 can be formed from polyurethane and treated and cut as described with respect to membrane 22 above.

FIG. 6 is a cross sectional view of filter 122 taken from FIG. 5. As shown in both FIGS. 5 and 6, filter 121 is in an expanded position. As can be seen in FIG. 6, spaced at approximately 90.degree. around frame 124 are for bending set points 125. Frame 124 can be bent at these points as described in more detail below to collapse filter 121 for delivery. Preferably, frame 124 is heat set to assume the expanded configuration shown in FIGS. 5 and 6 when exposed to approximately body temperature. The number of set points 125 and tails 128 can vary without deviating from the scope of the present invention.

Figure 7:
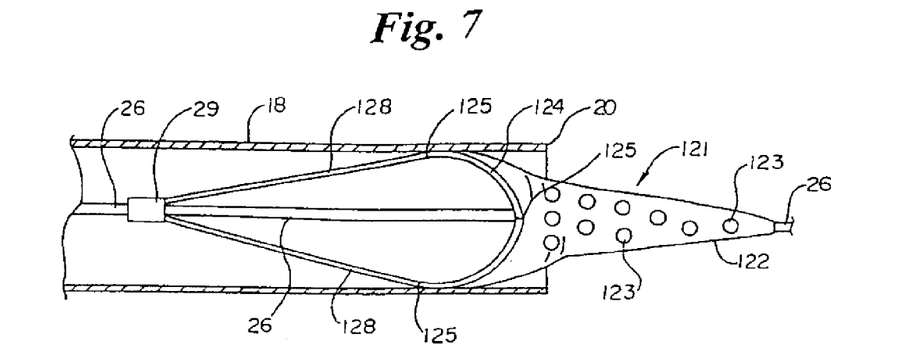
FIG. 7 is a side view of the filter of FIG. 5 disposed within a delivery catheter.
Figure 8:
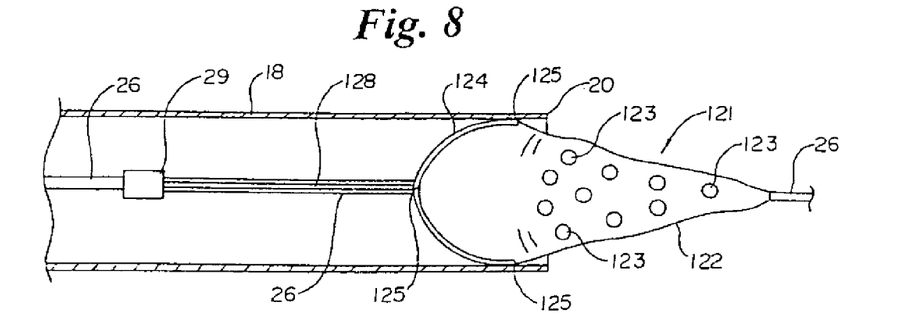
FIG. 8 is a side view of the catheter and filter of FIG. 7 rotated 90.degree. about the longitudinal axis thereof.

FIG. 7 is a side view of filter 121 disposed in delivery catheter housing 18. Shown in FIG. 7, bending set points 125 adjacent tails 128 are disposed proximally of the other two bending set points 125. FIG. 8 is a cross sectional view of housing 18 and filter 121 rotated 90.degree. about the longitudinal axis of wire 26 from the view shown in FIG. 7. By reference to both the views of FIG. 7 and FIG. 8, it can be appreciated that frame 124 bends proximally at the bending set points 125 connected to tails 128 and distally at the more distally disposed bending set points 125.

FIGS. 9-16 show various housing configurations described in the context of a delivery catheter. It can be appreciated by those skilled in the art that one or more of these housing configurations could be used for a retrieval catheter as well.

Figure 9:
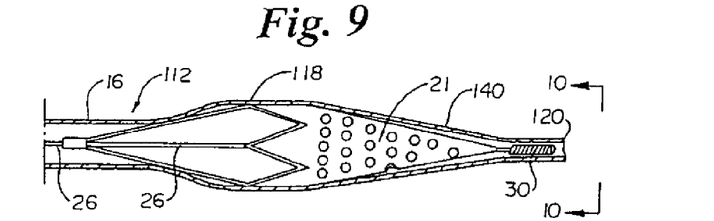
FIG. 9 is an alternate embodiment of a delivery catheter housing.
Figure 10:
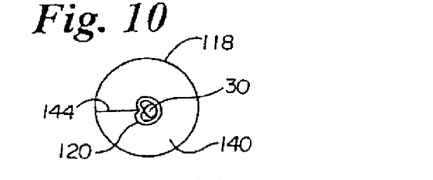
FIG. 10 is a distal end view of the housing of FIG. 9.

FIG. 9 is a cross sectional view of an alternate housing 118 having an atraumatic distal portion 140 which tapers distally over filter 21 to a distal tip 120. FIG. 10 is an end view of housing 11S of FIG. 9 showing a longitudinal slit 144 extending proximally from distal end 120. Tapered portion 140 is preferably disposed over filter 120 and then heat shrunk around filter 21. Those skilled in the art will appreciate that heat shrink material such as, for example, Teflon.®. would be suitable for forming taper portion 140.

Once housing 118 and filter 21 are positioned distally to the treatment site, filter 21 can be deployed by withdrawing housing 118 proximally. Slit 144 will allow portion 140 to open or unwrap as portion 140 is drawn proximally over filter 21. Slit 144 as shown in FIG. 10 only extends through tapered portion 140, however, a slit could extend to the proximal end of catheter 112. Those skilled in the art will appreciate that such a slit could be advantageously used to remove catheter 112 from a standard length wire 26.

Figure 11:
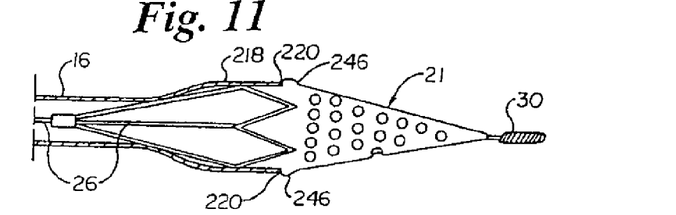
FIG. 11 is yet another alternate embodiment of the delivery catheter housing.

FIG. 11 is a cross sectional view of an alternate housing 218 having a distal end 220. The diameter of housing 218 has been set such that a portion 246 of filter 21 extends transversely over distal end 220 of housing 218. This provides a smooth atraumatic profile for advancement of housing 218 and filter 21.

Figure 12:
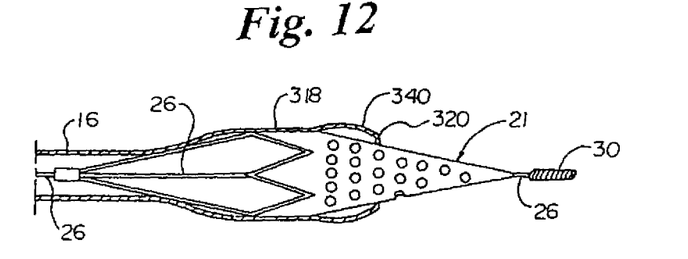
FIG. 12 is yet another alternate embodiment of the delivery catheter housing.

FIG. 12 is a cross section of yet an alternate embodiment of a housing 318 having a distal end 320 and a distal portion 340 curving transversely inward toward filter 21. The curve of distal portion 340 provides a desirably atraumatic profile for advancement of housing 318 and filter 21 to a treatment site.

Figure 13:
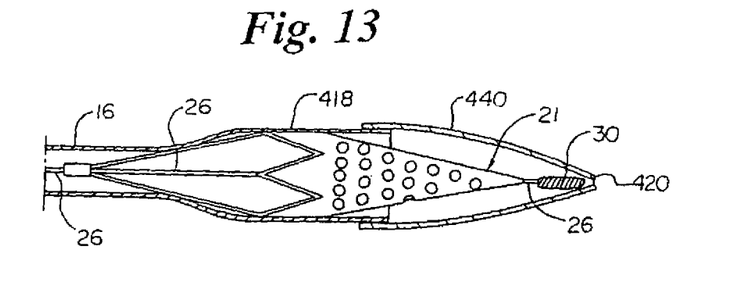
FIG. 13 is yet another alternate embodiment of the delivery catheter housing.

FIG. 13 is a cross sectional view of yet another embodiment of a housing 418. Housing 418 includes an elastomeric tapered portion 440. Tapered portion 440 of housing 418 has a distal end 420. Tapered portion 440 presents a desirable atraumatic profile for advancement of housing 418 and filter 21 to a treatment site. Once filter 21 and housing 418 are advanced distally of a treatment site, housing 418 can be withdrawn proximally from filter 21. As housing 418 is withdrawn proximately, elastomeric portion 440 stretches transversely such that filter 21 can exit distally from an opening at distal end 420.

Figure 14:
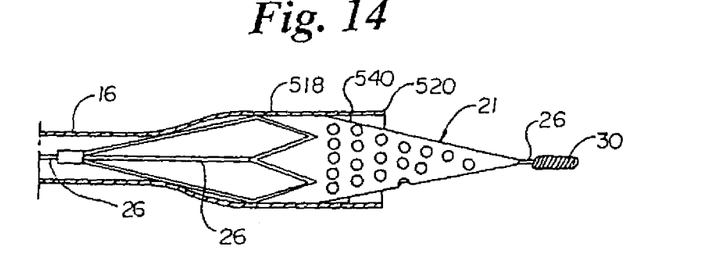
FIG. 14 is yet another alternate embodiment of the delivery catheter housing.

FIG. 14 is a cross sectional view of yet alternate embodiment of a housing 518 having a distal end 520. Housing 518 is substantially similar to housing 18, except that a highly flexible distal portion 540 is disposed at distal end 520. Highly flexible portion 540 can be formed from a material such as, for example, silicone rubber.

Figure 15:
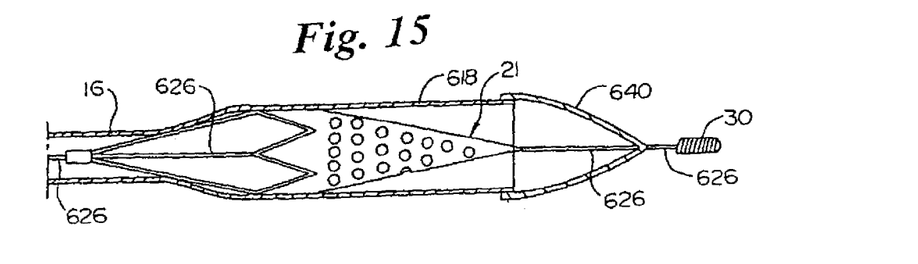
FIG. 15 is a view of an alternate embodiment of a housing for a delivery catheter in accordance with the present invention and a collapsible shell disposed over the distal end of the housing.

FIG. 15 is a cross sectional view of yet an alternate embodiment of a housing 618 having a distal end 620. A filter 21 is disposed therein. Filer 21 is placed on a wire 626 which extends sufficiently beyond the distal end of filter 21 and distal end 620 of housing 618 to allow a generally conical, elastomeric shell 640 to be placed over distal end 620 while being connected to wire 626. The generally conically shaped shell 640 provides a desirably tapered distal profile for advancement of housing 618 and filter 21 to a treatment site. Elastomeric shell 640 can be formed from a biocompatible material such as, for example, polyurethane or silicone rubber.

Figure 16:
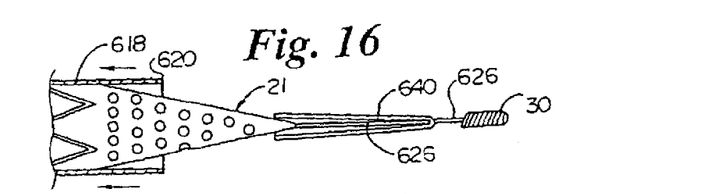
FIG. 16 shows the shell in a collapsed position.

As can be seen in FIG. 16, as housing 618 is withdrawn proximally from filter 21, elastomeric shell 640 will collapse around wire 626. It can be appreciated that the amount of elastic rebound, or the extent to which shell 640 collapses around wire 626 is a function of the modulus of elasticity of the material.

Figure 17:
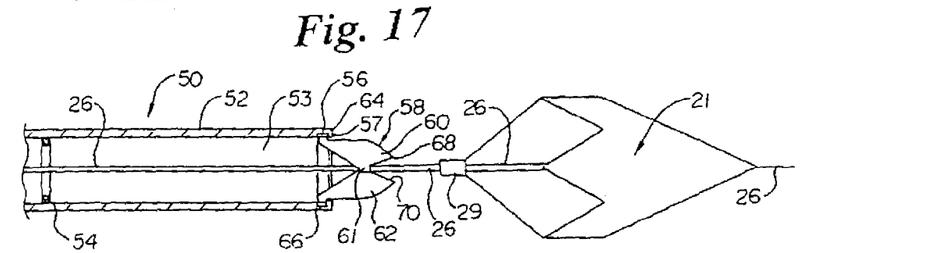
FIG. 17 is a partial cross sectional view of a retrieval catheter including a tip insert and filter.

FIG. 17 is a cross sectional view of a retrieval catheter 50 advanced on to wire 26 of a deployed filter 21. A retrieval catheter, such as catheter 50, is advanced to the treatment site to retrieve a filter 21 after an interventional procedure has been completed or the filter is no longer needed.

Catheter 50 has a housing 52 defining an inner lumen 53. Catheter 50 preferably has a shaft portion substantially similar to the embodiments described above with respect to catheter 12. Although a catheter such as a catheter 12 described above could be used to retrieve deployed filter 21, it is desirable that a retrieval catheter for filter 21 have both an atraumatic distal tip and a larger lumen for receiving a deployed filter 21. That is, lumen 53 preferably has a diameter greater than lumen 19 of housing 18. The inside diameter of lumen 53 is preferably between 3 F and 7 F and more preferably between 4 F and 6 F and, most preferably about 5 F. Housing 52 has a distal end 57.

A tapered insert 58 is disposed at distal end 57. Tapered insert 58 includes two scissor-like elements 60 and 62 which generally taper in a distal direction. Elements 60 and 62 are pivotally connected to wire 26 by pivot connector 61. Disposed at the proximal end of elements 60 and 62, respectively, are insert tabs 64 and 66 disposed within an insert receiving groove 56 of housing 52. The distal end of insert 58 includes a surface 68 on element 60 and a surface 70 on element 62 defining a stop receiving groove therebetween. Catheter 50 and insert 58 can be made from biocompatible materials known to those skilled in the art of catheter construction. Those materials include, among others those discussed above with respect to catheter 12.

Figure 18:
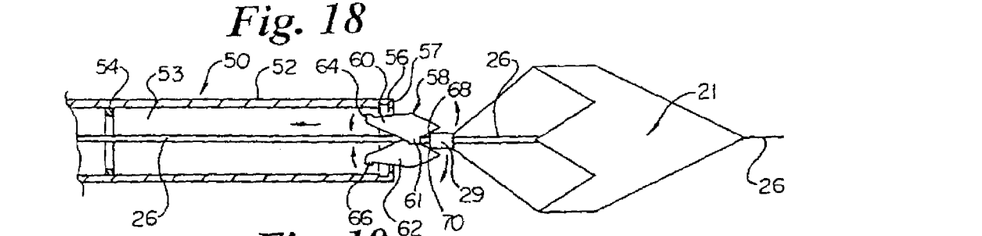
FIG. 18 is a view of the filter engaging the tip insert of FIG. 17.

FIG. 18 is a view of catheter 50 and filter 21 of FIG. 17, wherein filter 21 has been withdrawn proximally such that stop 29 has engaged insert 58. As can be seen in FIG. 18, stop 29 has engaged surfaces 68 and 70 of insert 58, elements 60 and 62 are pivoted about pivot connector 61 in the direction shown by the arrows. This has allowed tabs 64 and 66 to be displaced from insert receiving groove 56. It has thus been possible for insert 58, as well as filter 21, to have been moved proximally.

Figure 19:
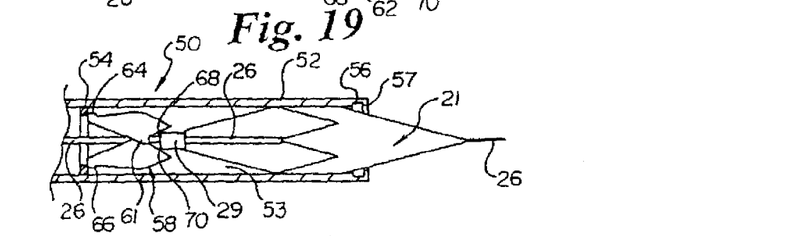
FIG. 19 is a view of the insert and filter of FIG. 17 withdrawn into the catheter.

FIG. 19 is yet another cross sectional view of catheter 50 and filter 21, wherein filter 21 has been partially collapsed and withdrawn into housing 52. Tabs 64 and 66 of insert 58 are engaging a stop ring 54 to limit further proximal movement of filter 21 relative to housing 52. In the configuration shown in FIG. 19, housing 52 and filter 21 can be withdrawn from a patient's body proximally.

Figure 20:
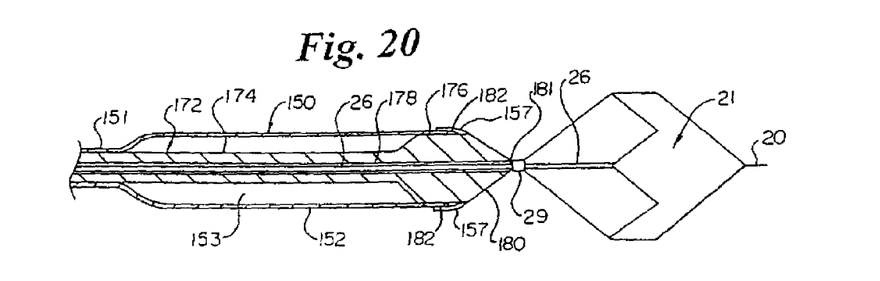
FIG. 20 is a partial cross sectional view of an alternate embodiment of a retrieval catheter, filter and retrieval catheter insert.

FIG. 20 is a cross sectional view of an alternate embodiment of a retrieval catheter 150. Retrieval catheter 150 includes a retrieval housing 152 and shaft 151. Housing 152 defines a retrieval lumen 153, and has a distal end 157. Catheter 150 is preferably made from materials the same or similar as those used to make catheter 50. Lumen 153 is also preferably sized similarly to lumen 53.

Disposed within catheter 150 is an insert catheter 172. Insert catheter 172 extends proximally from the proximal end of catheter 150 and is longitudinally slidable therein. Insert catheter 172 includes a shaft 174 having a transversely enlarged portion 176. Portion 176 preferably has a maximum outside diameter of approximately equal to, but less than, the inside diameter of lumen 153. Shaft 174 and portion 176 define a wire receiving lumen 178. Portion 176, as shown in FIG. 20, extends distally of distal end 157 of housing 152 and includes a tapered portion 180 tapering to a distal end 181. A sheath 182 extends proximally from taper portion 180 over and around distal end 157 of housing 152 to present a smooth tapered distal profile. An alternate embodiment of catheter 172 could be made without sheath 182.

One skilled in the art would appreciate the biocompatible materials available for construction of insert 172. Tapered portion 180 should be formed from material which is relatively soft and atraumatic. Sheath 182 is preferably formed from a relatively flexible biocompatible material, which is sufficiently flexible to deform as described in more detail below.

Figure 21:
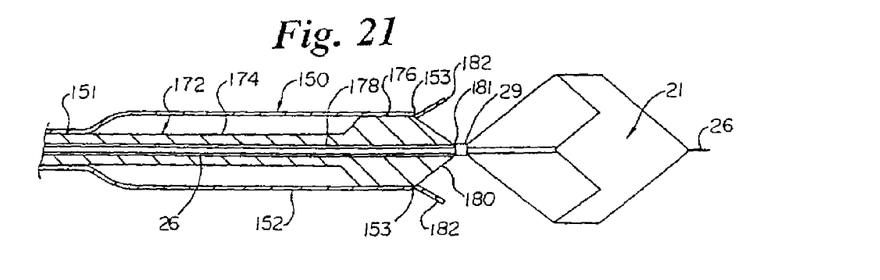
FIG. 21 is a view of the alternate embodiment of the insert of FIG. 20 partially withdrawn into the catheter.

FIG. 21 is a view of catheter 150 and filter 21 of FIG. 20, wherein filter 21 and insert 178 have been moved proximally such that sheath 182 has deflected in a distal direction. To complete the withdrawal of filter 21 from the vessel, insert 172 and filter 21 are moved proximally until filter 21 is collapsed and substantially drawn into housing 152.

Figure 22:
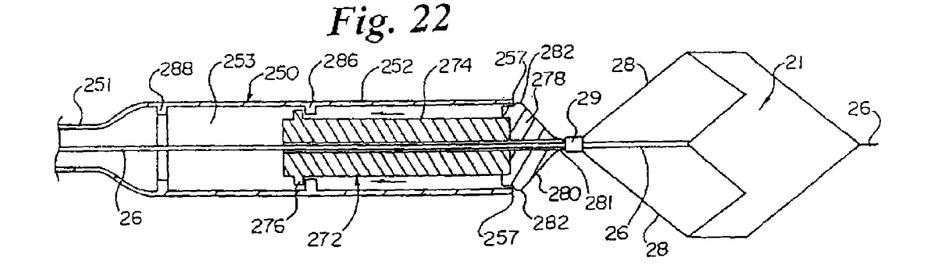
FIG. 22 is a partial cross sectional view of an alternate embodiment of a retrieval catheter, filter and retrieval catheter insert.

FIG. 22 is a cross sectional view of an alternate embodiment of a retrieval catheter 250 having a shaft 251 and retrieval housing 252. Housing 252 defines an inner lumen 253 and has a distal end 257. Disposed within housing 252, substantially proximally of distal end 257, is a distal bumper 286. Disposed still more proximally is a second and proximal bumper 288. Catheter 250 can be made from materials similar to those used to construct catheter 50. The inner diameter of lumen 253 is preferably similar to that of lumen 53.

Slidably disposed within lumen 253 is a housing insert 272. Insert 272 includes an elongate portion 274 having a bumper 276 disposed at the proximal end thereof. At the distal end of elongate portion 274 is an atraumatic tip 278 which is preferably formed from a soft atraumatic material adhered to elongate portion 274. Tip 278 preferably has a tapered end 280 extending to a distal tip 281. Extending transversely from tip 278 is a friction ledge 282 which engages distal end 257 of housing 252.

In use, when it is desired to retrieve deployed filter 21, catheter 250 is advanced over wire 26 until distal tip 281 engages stop 29. Catheter 250 is then pushed against pressing stop 29 and distal tip 281. The pushing force on catheter 250 is increased until friction ledge 282 deforms allowing insert 272 to move proximally in housing 252. Bumpers 286 can limit the distal travel of insert 272, bumpers 288 limit the proximal travel of insert 272 such that filter 21 will be at least partially collapsed and withdrawn into housing 252 for withdrawal from the body.

Figure 23:
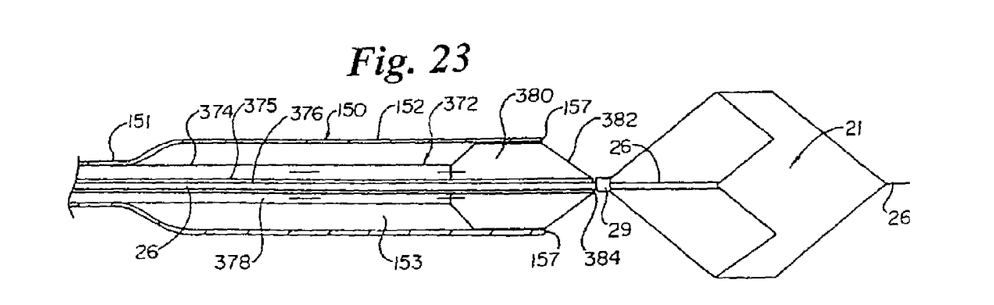
FIG. 23 is a partial cross sectional view of an alternate embodiment of a retrieval catheter, filter and retrieval catheter insert.

FIG. 23 is a cross sectional view of catheter 150 into which an alternate insert catheter 372 has been placed. Insert catheter 372 is similar to insert catheter 172 except that, rather than including a solid expanded portion 176, catheter 372 includes a balloon 380 disposed at the distal end of a shaft 374. An inner shaft 375 extends through shaft 374 and defines an annular inflation lumen 378 between shaft 375 and shaft 374 in fluid communication with balloon 380. Shaft 375 also defines a wire receiving lumen 376. Balloon 380 includes a tapered distal portion 382 which tapers to a distal end 384 sealably connected to the distal end of shaft 375. Those skilled in the art of balloon catheter construction will recognize the materials available for construction of balloon catheter insert 372.

In use, balloon 380 can be inflated and disposed at distal end 157 of housing 152 for advancement over wire 26. In this configuration, balloon 380 presents a tapered atraumatic profile desirable for advancement of catheter 150 to filter 21. Balloon 380 can then be deflated and balloon insert catheter 172 can be advanced over filter 21. Catheter 150 and filter 21 can then be withdrawn proximally from the patients body.

Figure 24:
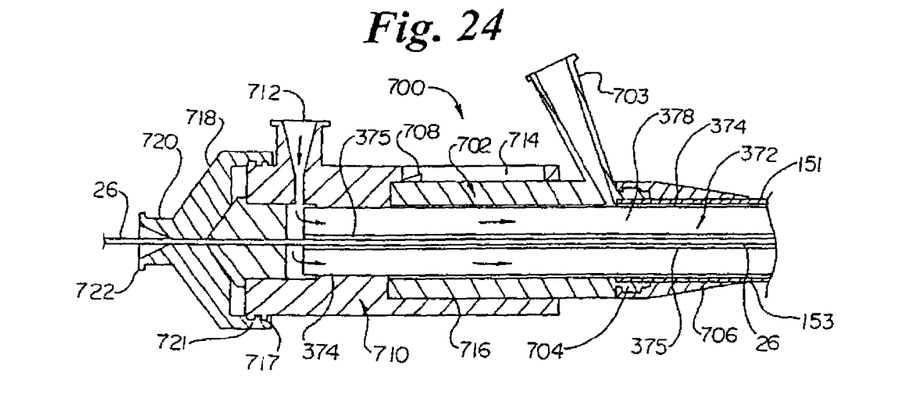
FIG. 24 is a view of a manifold for use with the embodiment of the retrieval catheter of FIG. 23.

FIG. 24 is a schematic, cross sectional view of a manifold for retrieval of a catheter 150 and balloon insert catheter 372. Manifold 700 includes a positive prep port portion 702 connected to the proximal end of catheter 152. The positive prep port portion 702 includes a positive prep port 703 in fluid communication with lumen 153 of shaft 151 of catheter 150. Positive prep portion 702 preferably includes at its distal end an interference connector 704 to connect a strain relief 706 thereto. Positive prep port portion 702 also includes a slide stop 708. One skilled in the art would recognize that manifolds can also be used for delivery catheters.

Manifold 700 includes a balloon prep portion 710 slidably disposed over positive prep portion 702 for longitudinal movement relative to portion 702. Balloon prep portion 710 includes a balloon prep port 712. Balloon insert catheter shaft 374 is connected to balloon prep port portion 710. Balloon prep port 712 is in fluid communication with balloon inflation lumen 378. Portion 710 also includes a stop slot 714 for receipt of stop 708 and a lumen 716 for slidable receipt of positive prep portion 702. A plurality of threads 717 are disposed at the proximal end of portion 710.

A collet 718 is disposed in part within portion 710 and in part between portion 710 and a guidewire clamp 720. Clamp 720 includes a plurality of threads 721 engageable with threads 717 of portion 710. Clamp 720 includes a guidewire prep port 722. Collet 718 can be tightened or loosened to hold guidewire 26 therein by threading or unthreading clamp 720 from portion 710. Collet 718 is shown clamped on wire 26 in both FIGS. 24 and 25.

Figure 25:
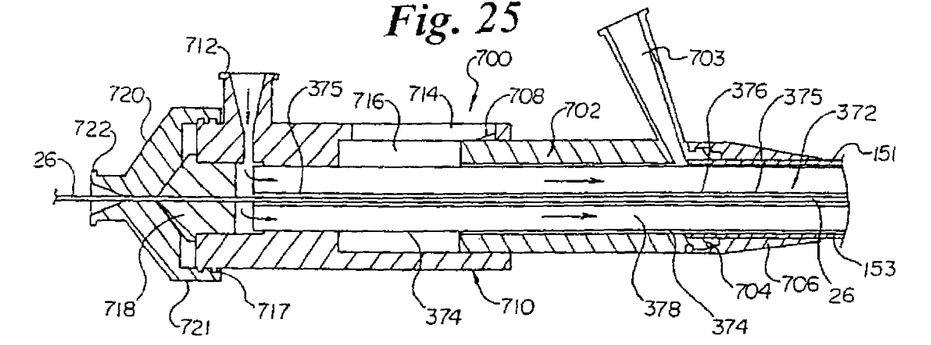
FIG. 25 is a cross sectional view of the manifold of FIG. 24 wherein the wire has been drawn proximally to withdraw the filter into the housing.

In use, balloon 780 can be advanced to distal end 157 of catheter 150 when portion 710 is advanced distally over positive prep portion 702 as shown in FIG. 24, such that stop 708 is at the proximal end of stop slot 714. Balloon 708 can inflated by way of inflation port 712. In this configuration, catheter 150 and insert 372 can be advanced over wire 26 to retrieve filter 21. Then collet 718 can be tightened to hold wire 26. Positive prep portion 702 is then pushed distally to capture filter 21. This will draw filter 21 into housing 152 of FIG. 23. Balloon 380 can be deflated prior to moving positive prep portion 702 distally. Stop 708 will be at the distal end of stop slot 714, as shown in FIG. 25, after housing 152 is moved over filter 21. Contrast media, saline or other fluids may be infused through positive prep port 703 as needed. Fluids could also be withdrawn through 703, if necessary. In the above embodiments, it has been shown that filter 21 remains stationary, while the various housing embodiments have been described as being advanced over the stationary filter 21 in order to retrieve said filter. Retrieving filter 21 into the housing, although a possible method of retrieval, is not preferred because of potential injury to the vessel lumen wall as the filter is dragged therein.

Figure 26:
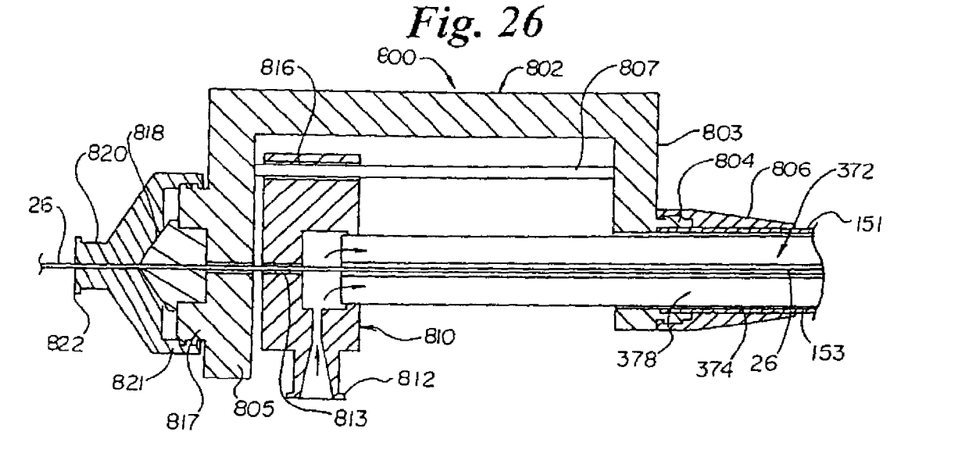
FIG. 26 is a cross sectional view of an alternate manifold in accordance with the present invention.

FIG. 26 is a cross sectional view of an alternate embodiment of a manifold 800. Manifold 800 includes a handle 802 including a distal arm 803 from which extends an interference connector 804 to connect a strain relief 806 thereto. Shaft 151 of catheter 150 is connected to arm 803. Handle 802 includes a proximal arm 805. Extending between proximal arm 805 and distal arm 803 is a slide rail 807. Mounted on slide rail 807 is a balloon prep portion 810. Balloon prep portion 810 includes a balloon prep port 812 in fluid communication with lumen 378 at catheter 372. Shaft 374 is connected to balloon prep portion 810. Wire 26 extends through portion 810 which is sealed around wire 26 by seal 813. Balloon prep portion 810 defines a rail lumen 816 such that balloon prep portion 810 is slidable longitudinally over rail 807. Proximal arm 805 also includes a threadable connector portion 817 threadably connected to a guidewire clamp 820. A collet 818 is disposed between arm 805 and clamp 820 which is threadably connected by threads 821 to threads 817. Clamp 820 includes a guidewire prep port 822.

In use, balloon 780 can be advanced to the distal end 157 of catheter 150 by advancing portion 810 distally over rail 807 to distal arm 803. Balloon 708 can be inflated by way of inflation port 812. In this configuration, catheter 150 and insert 372 can be advanced over wire 26 to retrieve filter 21. Collet 818 can then be tightened to hold wire 26. Handle 802 is then pushed distally to capture filter 21. This will draw filter 21 into housing 152. Balloon 380 can be deflated prior to moving handle 802 distally. Portion 810 will then be repositioned proximally adjacent arm 805. As described with respect to manifold 700, it is also possible to hold handle 802 stationary and move wire 26 distally to draw filter 21 into housing 152, however, this method is not preferred because of potential injury to the vessel lumen wall as the filter is dragged proximally.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the inven-

What is claimed is:

1. A filter assembly comprising:
 a catheter having a proximal section and a distal section, the distal section including a housing having an elastomeric distally tapered portion disposed about a distal end thereof;
 an elongated shaft disposed within a lumen of the catheter, the elongated shaft having a proximal section and a distal section including an atraumatic tip; and
 a filter fixedly coupled to the distal section of the elongated shaft, the filter including a filter frame actuatable between a collapsed position and an expanded position and a filter membrane disposed on a distal portion of the filter frame;
 wherein the elastomeric distally tapered portion of the housing provides an atraumatic profile for advancement of the housing and the filter to a treatment site.

2. The filter assembly of claim 1, wherein the elongated shaft comprises a guidewire.

3. The filter assembly of claim 1, wherein the elastomeric distally tapered portion is fixedly attached to the distal end of the housing.

4. The filter assembly of claim 1, wherein the elastomeric distally tapered portion stretches transversely to permit the filter to exit distally through an opening at the distal end of the elastomeric distally tapered portion as the catheter is withdrawn proximally relative to the filter.

5. The filter assembly of claim 4, wherein the opening is smaller than the atraumatic tip prior to stretching.

6. The filter assembly of claim 1, wherein the housing further comprises a tapered proximal portion.

7. The filter assembly of claim 6, wherein when the filter is disposed within the housing in the collapsed position, the filter frame is disposed adjacent a tapered proximal portion of the housing and at least a portion of the filter extends distally of the distal end of the housing.

8. The filter assembly of claim 7, wherein the elastomeric distally tapered portion surrounds the portion of the filter extending distally of the distal end of the housing and the atraumatic tip during advancement to the treatment site.

* * * * *